United States Patent [19]

Straub et al.

[11] Patent Number: 4,551,512

[45] Date of Patent: Nov. 5, 1985

[54] WATER-SOLUBLE POLYMERS HAVING A LOW HYGROSCOPICITY

[75] Inventors: Ferdinand Straub, Hockenheim; Axel Sanner, Frankenthal; Karl Seib, Weinheim; Siegfried Lang, Ludwigshafen, all of Fed. Rep. of Germany

[73] Assignee: BASF Aktiengesellschaft, Fed. Rep. of Germany

[21] Appl. No.: 597,665

[22] Filed: Apr. 6, 1984

[30] Foreign Application Priority Data

Apr. 8, 1983 [DE] Fed. Rep. of Germany ....... 3312668

[51] Int. Cl.[4] .................. C08F 218/04; C08F 218/08; C08F 220/20; C08F 226/10
[52] U.S. Cl. ...................................... 526/264; 424/70; 424/78
[58] Field of Search ................................ 526/258, 264

[56] References Cited

U.S. PATENT DOCUMENTS

| | | | |
|---|---|---|---|
| 3,445,566 | 5/1969 | Skoultchi | 424/47 |
| 3,743,715 | 7/1973 | Paris et al. | 526/264 |
| 3,775,537 | 11/1973 | Lehmann et al. | 526/258 |
| 3,927,199 | 12/1975 | Micchelli | 424/47 |
| 4,012,501 | 3/1977 | Farber | 424/47 |
| 4,112,215 | 9/1978 | Boessler | 528/503 |

*Primary Examiner*—Harry Wong, Jr.
*Attorney, Agent, or Firm*—Keil & Weinkauf

[57] ABSTRACT

Readily water-soluble, slightly hygroscopic terpolymers which consist of
- (a) from 10 to 40% by weight of vinylpyrrolidone,
- (b) from 20 to 50% by weight of vinyl acetate (VAc) or vinyl propionate and
- (c) from 10 to 40% by weight of hydroxyethyl acrylate, hydroxypropyl acrylate or hydroxyethyl methacrylate, which terpolymers are used as auxiliaries in the cosmetics and pharmaceuticals sectors.

2 Claims, No Drawings

WATER-SOLUBLE POLYMERS HAVING A LOW HYGROSCOPICITY

The present invention relates to N-vinylpyrrolidone (VP) copolymers which are water-soluble but only weakly hygroscopic and therefore do not tend to become tacky in moist air.

There are cases, for example binders and coating materials for tablets, where a polymer is required to have two mutually opposing properties, namely water-solubility on the one hand, and very low hygroscopicity on the other hand, ie. the tendency, in the dry state, to absorb moisture from the air is only very slight.

Since the two requirements are difficult to satisfy simultaneously, in many cases there is no option but to dispense with the water-solubility and to remedy this deficiency by using other solvents or solvent mixtures (cf. for example U.S. Pat. Nos. 3,445,566, 4,012,501 and 3,927,199) or to disperse the substances in water (cf. for example U.S. Pat. No. 4,112,215).

Vinylpyrrolidone copolymers are used in the pharmaceuticals and cosmetics sectors as, for example, tablet binders, coating materials and film formers. Polyvinylpyrrolidone (PVP) homopolymers have the disadvantage that they are hygroscopic, absorbing more than 26% of water at 75% relative humidity and 23° C. Since water-containing PVP adheres, the hygroscopic behavior of PVP leads to undesirable sticking together of the tablets, etc. in moist rooms or regions. Attempts have been made to prevent the adhesion by copolymerization of vinylpyrrolidone with, for example, vinyl esters, or by admixing water-repellent, non-polar substances, such as talc or stearyl alcohol. However, when excessively large amounts of water-repellent substances are incorporated as copolymerized units or admixed, the copolymer or the mixture is no longer water-soluble. The water-insoluble substances settle out and cause technical problems.

The conventional copolymers of N-vinylpyrrolidone with vinyl acetate are water-soluble only when the content of VP is more than 60% by weight, and they then absorb more than 18% of water as 75% relative humidity and 23° C.

It is an object of the present invention to provide a polymer which is readily soluble in water and does not tend to become tacky in moist air.

We have found that this object is achieved, in accordance with the invention, by terpolymers which consist of
  (a) from 10 to 40, preferably from 30 to 40, % by weight of N-vinylpyrrolidone,
  (b) from 20 to 50, preferably from 30 to 40, % by weight of vinyl acetate (VAc) or vinylpropionate and
  (c) from 10 to 40, preferably from 30 to 35, % by weight of hydroxyethyl acrylate, hydroxypropyl acrylate or hydroxyethyl methacrylate.

Copolymers having this composition are (when copolymerization is carried out correctly) readily water-soluble, absorb little water (less than 15% by weight at 23° C. and 75% relative humidity) and therefore do not tend to become tacky in moist air.

For the purposes of the present invention, correct polymerization is a copolymerization procedure such that, in spite of the large difference in the copolymerization parameters of the components (the vinyl esters are the slowest to copolymerize, the N-vinylpyrrolidone copolymerizes more rapidly and the acrylates undergo the most rapid copolymerization), the composition of the polymer not only corresponds to the overall proportions of the monomers used, but is also fairly uniform over the entire length of the polymer chains. It is known that this can be achieved by matching the rate of addition of either all the components or at least the rapidly copolymerizing components in the reaction space to the rate of copolymerization of the slowest components, so that the concentration of these increases only slightly, if at all, toward the end of the polymerization. Without this measure, the product obtained would not be a true copolymer (with a roughly statistical distribution of the components), but more or less a block copolymer. Such a copolymer would not have the advantageous properties of the copolymers according to the invention, and would not therefore be distinguished by the combination of water-solubility and low moisture absorption from the air.

The novel terpolymers are useful in the cosmetics and pharmaceuticals sectors, for example as hair-setting lotions and binders and/or coating materials for tablets, for achieving satisfactory coatings in the conventional film coating apparatuses and in the conventional granulation apparatuses.

In the Examples which follow, parts and percentages are by weight.

EXAMPLE 1

In a stirred flask equipped with a reflux condenser and two dropping funnels, 10% of a mixture of
(A) 210 parts of N-vinylpyrrolidone, 280 parts of vinyl acetate, 210 parts of hydroxyethyl acrylate and 250 parts of isopropanol and
(B) 5 parts of tert.-butyl perpivalate and 150 parts of isopropanol
is initially taken, and the mixture is boiled gently at 60° C. When polymerization has started, the monomers are added in the course of 7 hours and the peroxide in the course of about 9 hours, the internal temperature increasing to 80° C. The mixture is refluxed for a further 2 hours, after which the solvent (isopropanol) is expelled with steam, and the aqueous polymer solution is freeze-dried. The solid product is readily water-soluble and has a K value (according to H. Fikentscher, Cellulose-Chemie 13 (1932), 58–64 and 71–74) of 20, measured in a 2% strength aqueous solution at 20° C., and a water absorption of 13.1% at 75% relative humidity and 23° C.

EXAMPLES 2 TO 5

The polymerization is carried out by a procedure similar to that described in Example 1. The resulting polymers are readily water-soluble, their composition and water absorption from the air being shown in the Table below:

| No. | N—Vinylpyrrolidone parts | % | Vinyl acetate parts | % | Hydroxyalkyl acrylate parts | % | % water absorption at 75% relative humidity and 23° C. |
|---|---|---|---|---|---|---|---|
| 2 | 245 | 35 | 210 | 30 | 245 HEMA | 35 | 10 |
| 3 | 280 | 40 | 210 | 30 | 245 HPA | 30 | 14.8 |
| 4 | 230 | 33 | 230 | 33 | 230 HPA | 33 | 12.8 |

-continued

| No. | N—Vinyl-pyrrolidone parts | % | Vinyl acetate parts | % | Hydroxyalkyl acrylate parts | % | % water absorption at 75% relative humidity and 23° C. |
|---|---|---|---|---|---|---|---|
| 5 | 210 | 30 | 280 | 40 | 210 HPA | 30 | 11 |

HEMA = hydroxyethyl methacrylate
HPA = hydroxypropyl acrylate

USE EXAMPLES

Film coating

EXAMPLE 6

5 parts of the copolymer described in Example 5,
1.5 parts of a commercial red coating material consisting of a basic aluminum salt of 2,4,5,7-tetraiodofluorescein, 5.0 parts of talc and
88.5 parts of water.

1,250 parts of an aqueous suspension having the above composition are sprayed onto 5,000 parts of tablet cores and then dried to give smooth, glossy film tablets. The suspension can be sprayed on continuously with a high throughput. The addition of a plasticizer is not necessary.

The spraying conditions are as follows: the air feed is at 45° C., the spray pressure is 2 bar, and spraying is carried out continuously in a laboratory apparatus, 100 g of suspension being sprayed in the course of 25 minutes.

EXAMPLE 7a

The following formulation can be used in a procedure similar to that described in Example 6:
5 parts to the polymer described in Example 4,
4 parts of polyethylene glycol having a molecular weight of 6,000,
0.5 part of glycerol,
1.5 parts of the colored coating material of Example 6,
3.0 parts of titanium dioxide,
5.0 parts of talc and
81.0 parts of water.

EXAMPLE 7b 5 parts of the polymer described in Example 5,
1.5 parts of polyethylene glycol having a molecular weight of 6,000 and
93.5 parts of water.

Hair-setting lotion

EXAMPLE 8

3 parts of the terpolymer described in Example 5 and
97 parts of distilled water.

EXAMPLE 9

3 parts of the terpolymer described in Example 4,
0.5 part of a 40% strength aqueous solution of a copolymer consisting of 95% by weight of vinylimidazolium methochloride and 5% by weight of N-vinylpyrrolidone, and
96.5 parts of distilled water.

EXAMPLE 10

3.0 parts of the terpolymer described in Example 4,
30.0 parts of isopropanol and
67.0 parts of distilled water.

EXAMPLE 11

3.0 parts of the terpolymer described in Example 5,
0.5 part of the same 40% strength aqueous copolymer solution as in Example 9,
30.0 parts of absolute ethanol and
66.5 parts of distilled water.

Blow-drying lotions

EXAMPLE 12

0.7 part of the terpolymer described in Example 4 and
99.3 parts of distilled water.

EXAMPLE 13

0.7 part of the terpolymer described in Example 5,
0.5 part of the same 40% strength aqueous copolymer solution as in Example 9 and
98.8 parts of distilled water.

EXAMPLE 14

0.7 part of the terpolymer described in Example 5,
30.0 parts of isopropanol and
69.3 parts of distilled water.

EXAMPLE 15

0.7 part of the terpolymer described in Example 4,
0.5 part of the same 40% strength aqueous copolymer solution as in Example 9,
30.0 parts of absolute ethanol and
68.8 parts of distilled water.

Hair sprays

EXAMPLE 16

2.0 parts of the terpolymer described in Example 4,
38.0 parts of absolute ethanol and
60.0 parts of a mixture of $CFCl_3$ and $CF_2Cl_2$ in a weight ratio of 50:50.

EXAMPLE 17

2.0 parts of the terpolymer described in Example 5,
35.0 parts of methylene chloride,
33.0 parts of isopropanol and
30.0 parts of a mixture of propane and butane in a weight ratio of 40:60.

EXAMPLE 18

2.0 parts of the terpolymer described in Example 4,
35.0 parts of methylene chloride,
13.0 parts of absolute ethanol and
30.0 parts of a mixture of propane and butane in a weight ratio of 40:60.

Granulation experiments

EXAMPLE 19

I (90 parts of Al acetylsalicylate,
(75 parts of mannitol and
(10 parts of corn starch.

II 7 parts of the polymer of Example 5 (dissolved in 30 parts of $H_2O$) and
1.8 parts of a lubricant (a mixture of 1 part of Aerosil, 1 part of Ca arachinate and 8 parts of talc).

Mixture I is moistened thoroughly with II and then passed through a sieve having a mesh size of 0.5 mm, and the product is dried, passed once again through a sieve and then mixed with 1.8 parts of the lubricant.

When these granules are tableted, the resulting tablets have high strength and good disintegration properties.

We claim:
1. A water-soluble terpolymer which consists of
   (a) from 10 to 40% by weight of N-vinylpyrrolidone,
   (b) from 20 to 50% by weight of vinyl acetate (VAc) or vinyl propionate and
   (c) from 10 to 40% by weight of hydroxyethyl acrylate, hydroxypropyl acrylate or hydroxyethyl methacrylate.
2. A water-soluble terpolymer as claimed in claim 1, which is composed of
   (a) from 30 to 40% by weight of N-vinylpyrrolidone,
   (b) from 30 to 40% by weight of vinyl acetate or vinyl propionate and
   (c) from 30 to 35% by weight of hydroxyethyl acrylate, hydroxypropyl acrylate or hydroxyethyl methacrylate.

* * * * *